United States Patent [19]

Wu

[11] 4,234,510

[45] Nov. 18, 1980

[54] RECOVERY OF ACRYLONITRILE OR METHACRYLONITRILE BY CONDENSATION

[75] Inventor: Hsin C. Wu, Parma, Ohio

[73] Assignee: Standard Oil Company, Cleveland, Ohio

[21] Appl. No.: 367,840

[22] Filed: Jun. 7, 1973

[51] Int. Cl.³ .................. C07C 120/00; C07C 120/14; C07C 121/32

[52] U.S. Cl. .............................. 260/465.3; 260/465.9

[58] Field of Search ............................ 260/465.3, 465.9

[56] References Cited

U.S. PATENT DOCUMENTS

| | | | |
|---|---|---|---|
| 3,210,399 | 10/1965 | Krzemicki | 260/465.9 X |
| 3,459,639 | 8/1969 | Borrel et al. | 260/465.3 X |
| 3,462,477 | 8/1969 | Caporali et al. | 260/465.3 |
| 3,636,067 | 1/1972 | Lovett et al. | 260/465.3 |
| 3,636,068 | 1/1972 | Lovett et al. | 260/465.3 |

FOREIGN PATENT DOCUMENTS 1020088  2/1966  United Kingdom .

*Primary Examiner*—Joseph Paul Brust
*Attorney, Agent, or Firm*—David J. Untener; Herbert D. Knudsen; Larry W. Evans

[57] ABSTRACT

Acrylonitrile or methacrylonitrile found in the reactor effluent of the ammoxidation reaction of propylene or isobutylene is recovered by cooling the reactor effluent to a temperature of about 40° to about 100° C. using direct contacting cooling, preferably with an aqueous stream, to obtain a gaseous stream containing acrylonitrile or methacrylonitrile and cooling the gaseous stream using indirect contact cooling to condense at least some of the acrylonitrile or methacrylonitrile from the gaseous stream.

9 Claims, 1 Drawing Figure

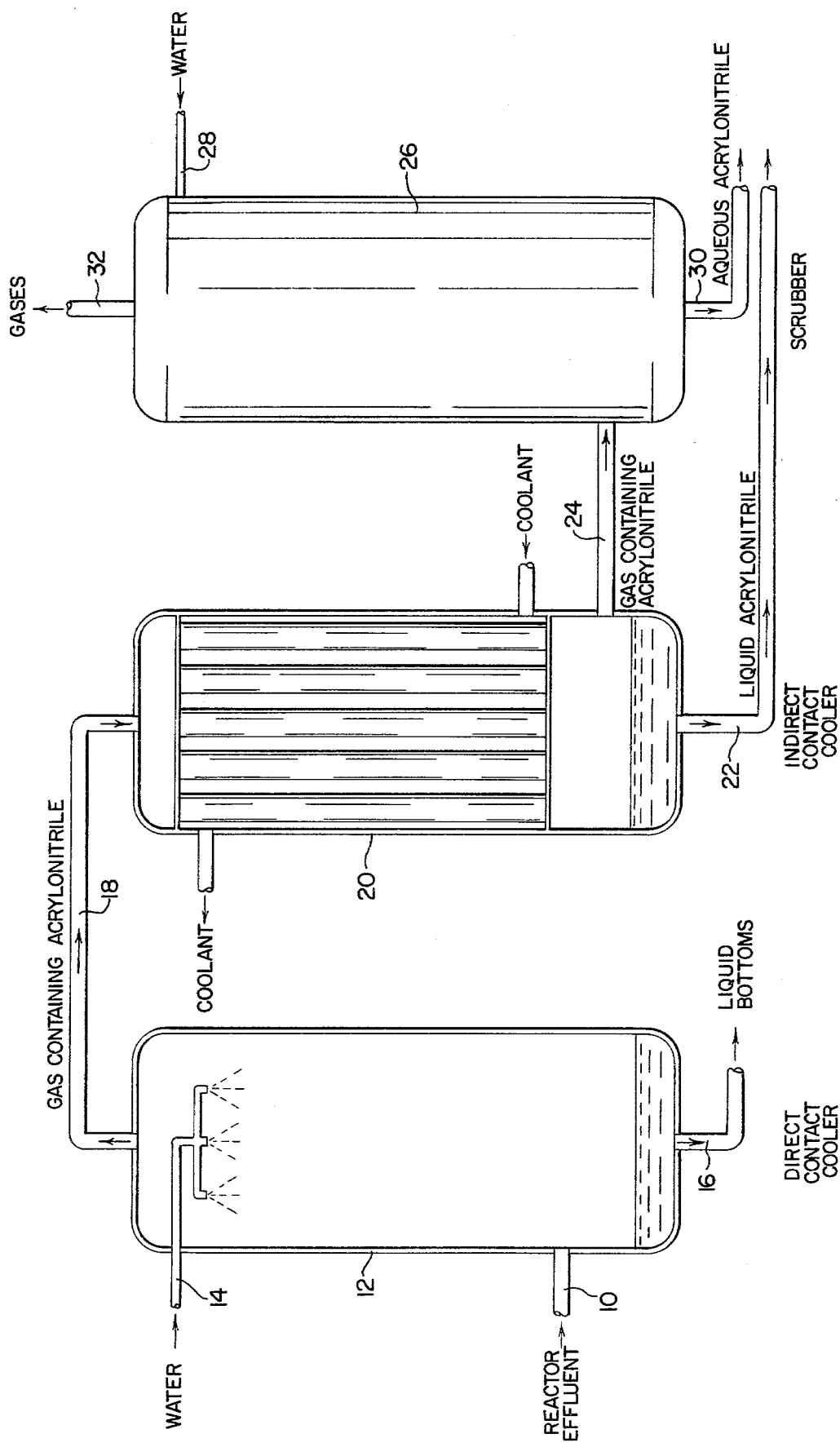

RECOVERY OF ACRYLONITRILE OR METHACRYLONITRILE BY CONDENSATION

BACKGROUND OF THE INVENTION

Recovery of acrylonitrile or methacrylonitrile produced by the ammoxidation of propylene or isobutylene on a commercial scale has been accomplished by quenching the reactor effluent with water and passing the gaseous stream containing acrylonitrile or methacrylonitrile resulting from the quench to an absorber where water and the gases are contacted in a countercurrent flow to remove all of the acrylonitrile or methacrylonitrile. A voluminous liquid stream is formed which is subjected to further recovery steps.

The present invention is directed toward increasing the efficiency of the recovery of acrylonitrile or methacrylonitrile while at the same time reducing the capital and operating expenses incurred in the construction and operation of the plant.

SUMMARY OF THE INVENTION

It has now been discovered in the process for the recovery of acrylonitrile or methacrylonitrile obtained in the reactor effluent of the ammoxidation reaction of propylene or isobutylene the improvement comprising cooling the reactor effluent to a temperature between about 40° and about 100° C. using direct contact cooling wherein a liquid is contacted with the reactor effluent to obtain a gaseous stream containing acrylonitrile or methacrylonitrile and cooling the gaseous stream obtained using indirect contact cooling to condense at least some of the acrylonitrile or methacrylonitrile from the gaseous stream. Use of the present invention reduces the initial capital investment required for the plant because the absorber can be reduced in size or essentially eliminated, and other recovery equipment can be substantially reduced in size because the volume of liquid is reduced. Also, the operating expenses of pumping large volumes of liquid to the absorber and throughout the recovery system is very significantly reduced.

The present invention is best understood by reference to the drawing.

DESCRIPTION OF THE DRAWING

The FIGURE shows a schematic representation of the process of the present invention as it applies to the recovery of acrylonitrile.

The reactor effluent from the ammoxidation of propylene is fed through conduit 10 into the direct contact cooler 12. In the direct contact cooler 12 water fed through line 14 is contacted with the reactor effluent to cool the reactor effluent to a temperature of about 40° to about 100° C. Polymers, ammonium sulfate and other condensible and soluble materials are collected and passed through line 16 to a waste treatment system or recycle. The temperature and pressure are maintained in such a manner that little or none of the acrylonitrile is condensed.

The gaseous overhead from the direct contact cooler 12 contains acrylonitrile. This gaseous overhead is fed through line 18 into indirect contact cooler 20. In the indirect contact cooler 20 the gas containing acrylonitrile is fed through chambers, such as tubes, wherein the inner surface of the chamber is cooled by a flow of coolant on the outer surface of the chamber. Contact between the cool inner surface of the chamber and the hot gas cools the gas to condense at least some of the acrylonitrile.

The condensed liquid consisting mainly of acrylonitrile is transferred through conduit 22 to further recovery and purification operations (not shown). The gaseous stream from the indirect contact cooler 20 passes through line 24 to a scrubber 26 where the remaining acrylonitrile is scrubbed from the gas by water flowing through conduit 28 into the scrubber. The water containing acrylonitrile is passed through line 30 to further recovery and purification operations (not shown). The gases not dissolved in the water pass overhead through conduit 32.

DESCRIPTION OF THE PREFERRED EMBODIMENTS

The central aspect of the present invention is that indirect contact cooling is employed to condense at least some of the acrylonitrile or methacrylonitrile from the reactor effluent. This condensation of acrylonitrile or methacrylonitrile reduces the load on the absorber column, thereby decreasing the capital and operating expenses attributable to the absorber. Furthermore the volume of the stream resulting from the process of the invention is substantially reduced. Thus, savings of capital and operating expenses are realized. This invention is especially applicable to plants having a capacity of more than a million kilograms per year production.

As noted, the invention entails a direct contact cooling of the reactor effluent followed by the condensation of at least some of the acrylonitrile or methacrylonitrile in an indirect contact cooler. The amount of unsaturated nitrile that is condensed in the indirect contact cooler may vary from a small amount to essentially all of the nitrile. In a preferred practice of the invention about 10 to about 90% of the nitrile fed to the indirect contact cooler is condensed, with the condensation of about 25 to 75% being especially economical. Of special interest in the invention is the condensation of more than 50% of the nitrile fed so that the amount of nitrile sent to the scrubber is less than half the total amount of nitrile recovered.

The amount of acrylonitrile or methacrylonitrile condensed in the present invention is broadly determined by the temperature and pressure conditions of the indirect cooler. Other variables such as the presence of azeotropic agents and entrainment of the nitriles in the gas flow remain relatively stable under normal operating conditions.

A primary variable controlling the condensation is the temperature. As the temperature is decreased, the amount of acrylonitrile or methacrylonitrile condensed is increased. Of course, the decrease of the temperature to very low levels required substantial indirect contact cooling. Determination of the desired temperature of operation is essentially a trade-off between the amount of nitrile condensed and the cost of the indirect cooling.

The optimum strategy, of course, is to condense as much acrylonitrile or methacrylonitrile as possible at minimum cost. The most economical operation will depend on the availability and cost of cooling capacity, capital and operating cost calculations and a number of other factors.

In the preferred practice of the invention, the temperature of the gas stream leaving the indirect contact cooler is between about 0° to about 30° C., with temperatures of between about 5° and 25° C. being especially preferred. Of course, there is an interdependence between the temperature and the pressure that must be taken into consideration in determining the desired temperature.

The pressure is an important variable in the determination of the amount of acrylonitrile or methacrylonitrile that is condensed—as the pressure is increased, more of the nitrile condenses. Since an increase in the pressure increases the equipment specifications and the capital cost, pressures of less than about 3 atmospheres gauge pressure are normally employed. For the preferred temperature conditions, pressures between about atmospheric pressure and one atmosphere gauge pressure are used.

The equipment used to carry out the invention is known. Direct contact systems have been employed to cool the temperature of the reactor effluent to temperatures of 40° to about 100° C. Indirect cooling systems are well known, and scrubbing towers for separating soluble components from a gas are known.

In a preferred practice of the invention, both the direct contact liquid and the scrubber liquid are aqueous streams containing at least about 80% by weight of water. Brine is a preferred indirect contact circulating fluid.

SPECIFIC EMBODIMENT

A computer simulation of the recovery of an acrylonitrile plant effluent was run. The given conditions were as follows: reactor effluent was cooled in the direct contact system to a temperature of about 90° C. at a pressure slightly higher than a half of an atmosphere gauge pressure. At about a half an atmosphere gauge pressure, the gas containing acrylonitrile from the direct contact cooler was cooled to a temperature of about 13° C.

The computer analysis indicated that about 42% of the acrylonitrile fed to the indirect coolers was condensed and approximately 58% of the acrylonitrile remained in the gaseous phase. Thus, the load going to the absorber was approximately cut in half.

In the same manner as shown by the example above, the temperature of the effluent gases from the indirect contact cooler could be reduced to 10° C. and a larger percentage of the acrylonitrile entering the indirect coolers will be condensed. Also, in the same manner as shown for acrylonitrile above, methacrylonitrile is recovered from the reactor effluent of the ammoxidation of isobutylene.

I claim:

1. In the process for the recovery of acrylonitrile or methacrylonitrile obtained in the reactor effluent of ammoxidation reaction of propylene or isobutylene, the improvement comprising cooling the reactor effluent to a temperature between about 40° and about 100° C. using direct contact cooling wherein an aqueous stream is contacted with the reactor effluent in such a manner that little or none of the acrylonitrile or methacrylonitrile is condensed to obtain a gaseous stream containing acrylonitrile or methacrylonitrile and cooling the gaseous stream obtained using indirect contact cooling to condense and separate about 10 to about 90% of the acrylonitrile or methacrylonitrile from the gaseous stream.

2. The process of claim 1 wherein about 25 to about 75% of the acrylonitrile or methacrylonitrile fed to the indirect cooler is condensed.

3. The process of claim 1 wherein more than 50% of the acrylonitrile or methacrylonitrile fed to the indirect cooler is condensed.

4. The process of claim 1 wherein the temperature of the gas leaving the indirect cooler is between about 0° and about 30° C.

5. The process of claim 1 wherein acrylonitrile is recovered.

6. The process of claim 1 wherein the pressure is less than about 3 atmospheres gauge pressure.

7. The process of claim 1 wherein the gaseous stream from the indirect contact cooling is fed to a scrubber which contacts a liquid with the gaseous stream to remove acrylonitrile from the gaseous stream.

8. The process of claim 7 wherein the liquid in the scrubber is an aqueous stream.

9. The process of claim 1 wherein the gaseous stream from the indirect contact cooling is fed to a scrubber for removing acrylonitrile or methacrylonitrile from the gaseous stream, and wherein the condensed, separated acrylonitrile or methacrylonitrile is recovered without passing said condensed separated acrylonitrile or methacrylonitrile to said scrubber.

* * * * *